United States Patent [19]

Zaiger

[11] Plant 4,553

[45] Jun. 24, 1980

[54] APRICOT TREE

[76] Inventor: Chris F. Zaiger, 537 Rosemore Ave., Modesto, Calif. 95351

[21] Appl. No.: 5,462

[22] Filed: Jan. 22, 1979

[51] Int. Cl.[2] ..... A01H 5/00
[52] U.S. Cl. ..... Plt./39
[58] Field of Search ..... Plt./39

*Primary Examiner*—Robert E. Bagwill
*Assistant Examiner*—James R. Feyrer

[57] ABSTRACT

A new and distinct variety of apricot tree which is dwarf in size (4 to 6 feet), dense and semi-upright in growth and being a regular and productive bearer of early maturing, medium size, firm, freestone fruit of good eating and keeping quality.

1 Drawing Figure

ORIGIN OF THE VARIETY

The present variety of dwarf apricot tree was originated by me at my experimental orchard located at Modesto, Calif., as an open pollenated seedling from an induced mutation by cobalt irradiation. The seedling, which was irradiated, was selected by me from my experimental orchard of a cross between Flaming Gold Apricot (U.S. Plant Pat. No. 2,822) and Gold Kist Apricot (U.S. Plant Pat. No. 2,826) and carried the field identification number of 2W26. The seedlings from the induced mutation were grown and maintained by me under close observation and the present variety which evidenced distinct desirable characteristics was selected for asexual reproduction.

ASEXUAL REPRODUCTION OF THE VARIETY

The present variety of dwarf apricot tree was asexually reproduced by budding as performed by me at my experimental orchard, located at Modesto, Calif. and shows that such reproductions and said characteristics run true to form and are established and transmitted through succeeding propagations.

SUMMARY OF THE VARIETY

The present variety of apricot tree is of dwarf size (4 to 6 feet), dense and semi-upright in growth and a regular and productive bearer of medium size, firm, freestone fruit; the dwarf apricot tree is further characterized by having close leaf nodes, short heavy branches, and a stocky trunk giving the appearance of an attractive ornamental that produces desirable early maturing fruit of good eating and keeping quality.

BRIEF DESCRIPTION OF THE DRAWING

The accompanying photographic illustrations show typical specimens of foliage and fruit of my new dwarf apricot variety, with exterior and sectional view of the fruit with the stone in place and a section of branch showing the length of leaf nodes, with the upper and lower surface of the foliage being illustrated.

DESCRIPTION OF THE VARIETY

The following is a detailed botanical description of the new and distinct variety of dwarf apricot tree, its foliage and fruit, base on observations of the specimens grown at Modesto, Calif. The color definitions (except those in common terms) referenced to Reinhold Color Atlas, by A. Korneruf and J. H. Wanscher.

Tree:
- *Size.*—Dwarf-approximately ¼ of normal size. Average height — 4–6 feet.
- *Vigor.*—Non-vigorous.
- *Form.*—Semi-upright.
- *Density.*—Dense.
- *Production.*—Productive.
- *Bearing.*—Regular bearer.

Trunk:
- *Size.*—Stocky.
- *Texture.*—Shaggy.

Branches:
- *Size.*—Stocky.
- *Texture.*—Shaggy.

Leaves:
- *Size.*—Medium. Average length — 2¾"–3¼". Average width — 1⅞"–2⅜".
- *Margin.*—Serrate.
- *Form.*—Ovate.
- *Petiole.*—Average length — ½"–¾".
- *Glands.*—Number 2 to 6. Primarily on petiole.
- *Color.*—Upper surface — (28-F-6 to 28-F-8). Lower surface — (28-E-5 to 28-E-6). Mid rib — (29-C-6).

Flower buds:
- *Size.*—Medium to small.
- *Shape.*—Medium to short.

Flowers:
- *Blooming period.*—Feb. 18, 1976 to Mar. 2, 1976. Varies from year to year due to weather conditions.
- *Size.*—Medium.
- *Color.*—Light pink — fades to white at pedal fall.
- *Pubescent.*—Present.

Fruit:
- *Maturity when described.*—Eating ripe. Date of first picking May 29, 1976. Date of last picking June 5, 1976.
- *Size.*—Medium. Axial diameter — from 1¾" to 2". Transverse diameter in suture plane - from 1⅞" to 2 1/16". Diameter measured at right angles to suture plane - from 1¾" to 2".
- *Form.*—Usually symmetrical. Globose.
- *Suture.*—Usually extends from base to apex. Terminates at blossom end.
- *Cavity.*—From round to slightly elongated at suture plane. Depth — from ⅛" to 3/16". Breadth — from ¼" to ⅜".

*Apex.*—Rounded to slightly depressed.

Skin:

*Thickness.*—Thin.

*Tendency to crack.*—None.

*Down.*—Scant — short.

*Color.*—Apricot yellow to cadmuim orange (5-B-6 to 5-A-8).

Flesh:

*Texture.*—Firm. Fine.

*Ripens.*—Even.

*Flavor.*—Subacid to mild.

*Eating quality.*—Good.

*Color.*—Light orange to deep orange (5-A-7 to 5-A-8).

Stone:

*Type.*—Free.

*Size.*—Small to medium. Average length — $\frac{7}{8}''$. Average breadth — $\frac{3}{4}''$. Average thickness — $\frac{1}{2}''$.

*Tendency to split.*—None.

*Color.*—Light brown - (6-C-5).

Use: Home and local market.

Keeping quality: Good.

The dwarf apricot tree and its fruit herein described may vary in slight detail due to climatic and soil conditions under which it may be grown; the present description being of the variety grown in my experimental orchard at Modesto, Calif.

I claim:

1. A new and distinct variety of apricot tree of dwarf size, dense, semi-upright in growth and being regular and productive bearer of early maturing, medium size, freestone fruit of good eating and keeping quality; the tree is further characterized by having close leaf nodes, short heavy branches and a stocky trunk giving the appearance of an attractive ornamental.

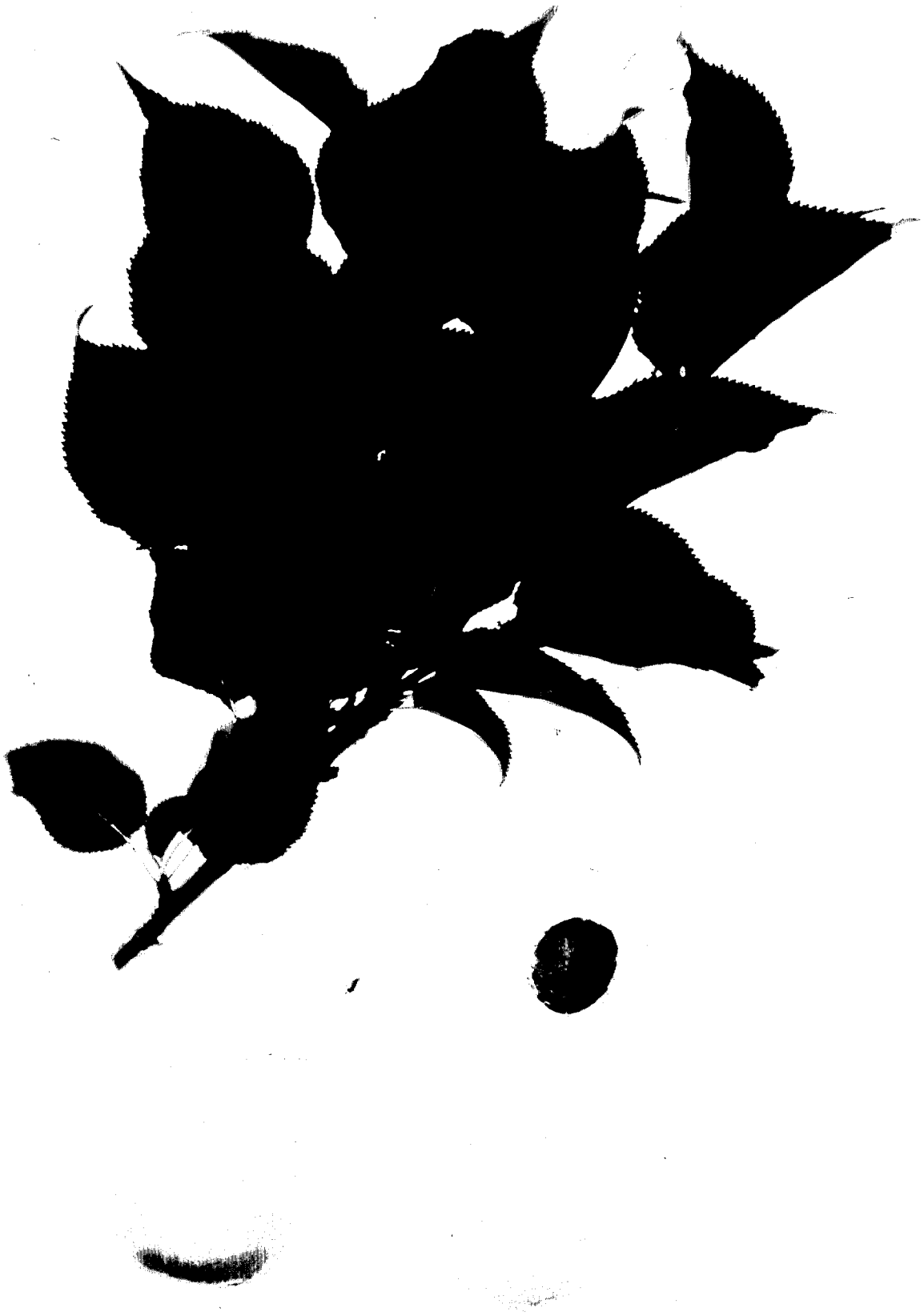

* * * * *